United States Patent [19]
Lawrence et al.

[11] Patent Number: 5,563,033
[45] Date of Patent: Oct. 8, 1996

[54] DETECTION OF INDIVIDUAL GENE TRANSCRIPTION

[75] Inventors: Jeanne B. Lawrence, Mapleville, R.I.; Carol V. Johnson, Stowe; Yigong Xing, Northborough, both of Mass.

[73] Assignee: The University of Massachusetts Medical Center, Worcester, Mass.

[21] Appl. No.: 23,953

[22] Filed: Feb. 26, 1993

Related U.S. Application Data

[63] Continuation-in-part of Ser. No. 832,667, Feb. 6, 1992, abandoned, which is a continuation of Ser. No. 257,066, Oct. 18, 1988, abandoned, which is a continuation-in-part of Ser. No. 790,107, Oct. 22, 1985, abandoned.

[51] Int. Cl.$^6$ .................................................. C12Q 1/68
[52] U.S. Cl. ................. 435/6; 435/810; 436/501; 536/22.1; 536/23.1; 536/24.3; 536/24.31; 536/24.32; 935/77; 935/78
[58] Field of Search ................. 435/6, 810; 436/501; 536/22.1, 23.1, 24.3, 24.31, 24.32; 935/77, 78

[56] References Cited

U.S. PATENT DOCUMENTS

| | | | |
|---|---|---|---|
| 4,888,278 | 12/1989 | Singer et al. | 435/6 |
| 5,225,326 | 7/1993 | Bresser et al. | 435/6 |

OTHER PUBLICATIONS

Xing et al., Science, vol. 259, Feb. 26, 1993, pp. 1326–1330.
Carter et al., Science, vol. 259, Feb. 26, 1993, pp. 1330–1335.
Xing et al., Trends in Cell Biology, vol. 3, No. 10, Oct. 1993, pp. 346–353.
Xing et al., J. Cell Biology, 115, No. 3, Part 2, Nov. 1991, p. 372A, Abstract No. 2162.
Lawrence et al., Cell, vol. 57, No. 3, May 5, 1989, pp. 493–502.
Carter et al., J. Cell Biology, vol. 115, No. 5, Dec. 1991, pp. 1191–1202.
Raap et al. (1991) Eapt. Cell Res., V. 197, pp. 319–322.

Primary Examiner—W. Gary Jones
Assistant Examiner—Ardin H. Marschel
Attorney, Agent, or Firm—Fish & Richardson P.C.

[57] ABSTRACT

In situ hybridization methods for assessing, determining or observing the RNA produced by transcriptionally active genes. In one embodiment, the methods allow simultaneous observation of the gene and its transcripts in a spatially correlated manner. As the in situ hybridization methods have established their ability to maintain the targeted mRNA at the site of its transcription, it can be determined which genes are being expressed and the level of expression can be quantitated.

8 Claims, 3 Drawing Sheets

(2 of 3 Drawing Sheets in Color)

DETECTION OF INDIVIDUAL GENE TRANSCRIPTION

This application is a continuation-in-part of U.S. Ser. No. 07/832,667; filed Feb. 6, 1992; now abandoned, which is a continuation of U.S. Ser. No. 07/257,066; filed Oct. 13, 1988; now abandoned, which is a continuation-in-part of U.S. Ser. No. 06/790,107, filed Oct. 22, 1985, now abandoned.

FIELD OF THE INVENTION

The present invention relates to methods for in situ hybridization and in particular to methods of in situ hybridization for evalluating the spatial organization of transcription, the transcriptional activity of specific genes and the distribution and processing of specific mRNAs in intact cells.

BACKGROUND OF THE INVENTION

The site of RNA processing and the spatial relationship between RNA processing and transcription in mammalian nuclei have not previously been established and there has been a long-standing interest in determining these parameters within the cell nucleus. There is evidence for and against the cotranscriptional splicing of precursor mRNAs. A. L. Beyer and Y. N. Osheim (*Semin. Cell. Biol.* 2, 131 (1991)) have shown that nascent transcripts in Drosophila are associated with spliceosomes, and in some cases, the spliceosome and nascent transcripts can be directly visualized by electron microscopy. In contrast, J. K. Nevins (*Annu. Rev. Biochem.* 52, 441 (1983)) and others have shown that the unspliced transcripts in mammalian cells can be isolated in the poly(A) fraction, indicating that splicing is posttranscriptional.

Previous studies attempting to determine whether or not mRNA transcripts in mammalian cells are localized at the site of transcription or are free to diffuse within the nucleus after synthesis are contradictory. Those studies which have reported localized loci of RNAs have been unable to establish the significance of these localizations. Highly localized nuclear "tracks" of specific viral mRNAs have been observed by fluorescence microscopy in chromatin-depleted nuclear matrix extracts (J. B. Lawrence, R. H. Singer and L. M. Marselle. *Cell* 57,493 (1989); Y. Xing and J. B. Lawrence. *J. Cell Biol.* 112, 1055 (1991)). Several viral RNAs have been observed to localize at only one or two sites within the nucleus (J. B. Lawrence, et al. (1989), supra; J. B. Lawrence, L. M. Marselle, K. S. Byron, J. L. Sullivan and R. H. Singer. *Proc. Natl. Acad Sci. USA* 87, 5420 (1990); A. Raap, et al. *Exp. Cell Res.* 197, 319 (1991)), but this observation is in contrast to microinjected globin RNA which appears to diffuse within the nucleus. Lawrence, et al. (1990) speculate that these tracks might represent sites of transcription, but cannot rule out other functions due to the hybridization protocols used. Although these studies demonstrated loci of RNA in the cell, their function could not be determined, e.g., whether they represented sites of transcription, sites of RNA processing, sites of RNA transport, or some other cellular function. Further, they could not spatially correlate the foci to any particular active genes. Total nuclear polyadenylate RNA (poly(A) RNA) has been shown to accumulate in 20 to 50 discrete "transcript domains" which coincide with the location of small nuclear ribonucleoproteins (snRNPs) (K. C. Carter, K. L. Taneja and J. B. Lawrence. *J. Cell Biol.* 115, 1191 (1991)). These snRNPs have previously been reported to exhibit a clustered nuclear distribution coincident with the spliceosome assembly factor SC-35. Although the association of poly(A) RNA with snRNPs in these studies was observed using hybridization of probes to DNA and mRNA in the same cell, it was not possible to make any conclusions concerning spatial correlation of transcription and processing of a specific RNA with expression of a specific gene because the DNA-specific probe was directed to untranscribed centromere DNA and the mRNA-specific probe oligo(dT) hybridized to total mRNA.

In the parent application U.S. Ser. No. 07/837,667, cytogenetic preparations were primarily used for the in situ hybridizations. One example (neu oncogene detection) uses fixed cells as in the present invention. The cytogenetic preparation methods degrade nuclear RNA and are therefore not useful in the present invention, which is directed to detection of nuclear RNAs and to simultaneous detection of nuclear DNA and RNA. Although the parent application states that DNA and RNA can be detected simultaneously, this refers only to hybridization under conditions which are permissive for both. The practitioner therefore is unable to distinguish DNA hybridization from RNA hybridization under these conditions. The EBV viral RNA detected in cytogenetic preparations in the parent application accumulates at abnormally high levels in the nucleus and is exceptionally stable. This RNA is produced from a latent viral infection and very little, if any, is transported to the cytoplasm and expressed. This EBV RNA was therefore unusually resistant to the cytogenetic preparation procedure and was detectable using the previously disclosed in situ hybridization methods. It was subsequently discovered, however, that these methods were not suitable for detection of the majority of mRNAs, which are less abundant and less stable than EBV RNA in that particular cell line. The present invention improves and extends those methods to detection of the relatively nonabundant and generally unstable specific nuclear RNAs, which are the products of expression and include most cellular genes and all protein coding genes.

Although the advantages of observing expression of a selected gene in intact cells (i.e., by in situ hybridization) have long been recognized, prior art hybridization methods have been unable to accomplish this, in part due to the lack of available techniques for specific staining of DNA and RNA in the same cell while preserving both the probe signals and the spatial relationship of the transcript and its active gene. The present invention for the first time provides methods for visualizing the intranuclear distribution of specific RNAs correlated to expression of a particular gene, relating this distribution to sites of transcription and processing and identifying larger domains of RNA transcription and processing enriched in polyA RNA and splicing factors. These studies have also established for the first time that mRNA transcripts in mammalian cells are localized at the site of transcription and processing and are not free to diffuse in the nucleus after transcription as some previous studies have suggested. Not only can expression patterns of a selected gene and the distribution of transcripts be identified, the present methods also for the first time allow comparison of the expression of specific alleles of a selected gene (gene imprinting). That is, unless the alleles express RNAs which are sufficiently different to alter hybridization to a probe, conventional in situ hybridization methods which target cytoplasmic RNA (and conventional filter nucleic acid hybridizations as well) are incapable of distinguishing allelic variants at the nucleic acid level. Using probes specific for the maternal or paternal chromosome and the RNA produced by the gene of interest according to the present methods, however, the practitioner can identify expression of an allele spatially correlated to either the maternal or paternal chromosome. Similarly, other genetic mutations which do not affect the mRNA enough to alter conventional hybridization to a probe may effect the distribution, processing or expression level of the RNA at the cellular level, and these abnormalities may also be detected using the present methods.

Applicants have also demonstrated analysis of the distribution of a specific viral RNA as a means for determining whether an infection is latent or productive. Using the present in situ hybridization methods for detection of EBV-specific RNA, the nucleus of cell latently infected with a single integrated copy of the virus shows a single, very long RNA track present only in the nucleus. A productive infection, in contrast, shows RNA-specific signals in both the nucleus and cytoplasm.

Although techniques for detection of single copy genes by in situ hybridization are available, the low abundance RNAs in the cytoplasm have remained below the limits of detection and sensitivity of non-isotopic methods. It was therefore especially unexpected that the present methods would increase the sensitivity and stability of in situ hybridization to a point where the very low abundance, labile mRNAs which had previously been undetectable in the cytoplasm could be detected in the nucleus. One significant example is dystrophin mRNA (0.01% of mRNA; J. Chelly, J. C. Kaplan, P. Maire, S. Gautron and A. Kahn. *Nature* 333,858. (1988)), which has been detected by the present methods of in situ hybridization but was previously undetectable in the cytoplasm. The dystrophin gene is carried on the X chromosome, one homologue of which is inactivated, consistent with detection of the dystrophin RNA as a single track. This result may be due to the fact that the instant methods maintain the targeted RNA in highly localized foci or tracks, thus increasing sensitivity by increasing the concentration of nonabundant mRNAs at a given cellular site. The inventive methods may also be used for detection of expression of exogenous gene sequences. The capability of assessing the level of expression of a gene is particularly useful for exogenous genes because they are often not expressed at normal levels and expression levels are often dependent on the site of integration.

SUMMARY OF THE INVENTION

The instant invention provides methods for assessing, determining or observing gene expression in situ. These methods for the first time allow the practitioner to correlate expression of a selected mRNA with a particular gene or locus in the nucleus of the intact cell by simultaneously observing an active gene and the mRNA transcribed from it. These methods make it possible to determine, by in situ hybridization, which copies of a gene present in the nucleus are being expressed and the level of expression of an active gene. Further, by selecting appropriate probes, processing and distribution of specific RNAs within the nucleus can be evaluated. These advantages have been made possible by the discovery of methods for in situ hybridization (including permeabilization and fixation of cells) which preserves labile nuclear RNAs, preserves the signal of hybridized RNA-specific nucleotide probes during in situ hybridization of DNA-specific probes and stabilize the RNA at the site of transcription. These inventive methods have provided the means for identifying the nature and function of the RNA tracks previously observed, which is the basis for the instant analysis of individual gene expression in situ. Further, the inventive methods provide means for determining the nuclear distribution of a specific RNA and evaluating RNA processing in ways which were not previously possible.

The present methods extend and modify the methods for preservation and detection of nuclear RNA and DNA in situ described by J. B. Lawrence, C. A. Villnave and R. H. Singer. *Cell* 52, 61 (1988), J. B. Lawrence, et al. (1989) supra, Y. Xing, et al. (1991) supra and K. C. Carter, et al. (1991) supra, to allow specific staining of both RNA and DNA in the same cell without loss of either the probe signal or the spatial relationship of the transcript and its corresponding gene. In one embodiment, the in situ hybridization methods employ the following steps: 1) permeabilization of the nucleus while controlling and minimizing degradation due to cellular components such as RNase's which are released during this process, 2) fixing the cells with a fixative such that the nucleus remains penetrable by labeled nucleotide probes and the nucleic acids are preserved and retained within the cell, 3) hybridizing with an RNA-specific probe under conditions in which the DNA is not denatured, 4) fixing the cells a second time to preserve the signal from any RNA hybrids formed during subsequent DNA hybridization steps, 5) denaturing the DNA, and 6) hybridizing with a DNA-specific probe. In a second embodiment, following preparation of the cells as in steps 1 and 2 the DNA and RNA targets are cohybridized in a single reaction step to probes showing a specific spatial association under conditions in which the DNA is denatured.

DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1 shows the location of fibronectin RNA track relative to sites of transcription and splicing.

FIG. 3 shows the fluorescence hybridization analysis of transgene DNA and RNA as described in Example 4.

DETAILED DESCRIPTION OF THE INVENTION

The inventive methods are useful for determining sites of specific RNA transcription, the level of transcription and the distribution and processing of transcripts in a cell. Detection of specific nuclear RNAs and DNAs by hybridization in an intact cell in a manner which preserved the RNA-specific signal and retains the target RNA at the site of transcription was not previously possible. Initially, the present in situ hybridization methods included hybridization of labeled probes to a gene (DNA) and its corresponding mRNA within the same cell. For convenience, this methodology is referred to herein as "simultaneous" hybridization of DNA and RNA. However, this term is intended to mean that the result of the hybridization is a cell in which both DNA and RNA are hybridized to probes which provide separately distinguishable signals. As described in more detail below, the steps themselves may either involve cohybridization of DNA and RNA to specific probes in a single reaction step or, alternatively, sequential hybridization to the RNA-specific probe followed by hybridization to the DNA-specific probe. As the inventive simultaneous hybridization methods have now established that the stained RNA resulting from these hybridizations is spatially correlated with its corresponding active genes, it will be readily appreciated that in some circumstances it will only be necessary to stain the RNA tracks to obtain the desired information. For example, if the number of copies of a gene in a cell is known and it is desired to determine how many of these copies are being expressed, it may not be necessary to visualize the gene itself with a DNA-specific probe. In such an application, the practitioner may stain only for the desired mRNA as taught herein and determine how many tracks are present in relation to the known number of copies of the gene. Applicants methods have provided the essential knowledge which permits the earlier studies described above to be interpreted unambiguously, i.e., that the RNA tracks previously observed identify sites of transcription (genes). See Lawrence, et al. (1990) and (1989), supra.

The simultaneous hybridization methods of the invention employ at least two nucleotide probes tagged with detectable labels as is known in the art. The preferred method is fluorescent in situ hybridization in which the probes are tagged with fluorescent labels. A first DNA-specific probe is selected to specifically hybridize to DNA sequences associated with a selected gene. As used herein, the term "associated with a selected gene" denotes a part of the coding or noncoding regions of the gene, or a sequence linked to the gene which as a result of proximity or chromatin packaging is sufficiently close to the gene to serve as an effective marker for the location of the gene. The DNA-specific probe may also be selected so as to hybridize only to the transcribed strand of the DNA in the coding region of the gene, thereby preventing non-specific hybridization to the mRNA transcript. Specific hybridization is defined as hybridization to the DNA sequence without substantial hybridization to non-targeted gene or RNA sequences, or substantial hybridization to the RNA which is to be detected. Substantial hybridization to non-specific nucleic acid sequences is a level of hybridization which results in sufficient background or non-specific signal from the label to obscure or confuse detection of the desired specific signal. To optimize spatial resolution between the gene and minimize cross-hybridization to its transcript, the DNA-specific probe may be selected from the 5' or 3' untranscribed sequences of the selected gene or some other linked untranscribed sequence which upon DNA-specific hybridization and staining appears adjacent to the signal from RNA-specific hybridization. Sequences separated from the gene or RNA track by as much as approximately 3 megabases (about 2 μm) may be used, as they can appear close to the RNA signal due to packaging of the chromatin (see the YAC-specific DNA probe, below). It was not previously recognized that such distant sequences could be useful for marking or identifying a site of RNA transcription, and they have not previously been used in this manner. Alternatively, the DNA-specific probe may target a sequence within the transcribed portion of the gene or the same sequence targeted in the RNA. For certain applications, such as identification of expression of maternal vs. paternal alleles, the DNA-specific probe may hybridize to a sequence removed from the site of gene transcription which is a specific marker for the chromosome or for a specific homologue of the chromosome.

The RNA-specific nucleotide probe is selected to hybridize to the mRNA transcript of the selected gene without substantial hybridization to non-targeted DNA or RNA sequences. This specificity is the result of the hybridization protocol, as the probe would otherwise hybridize to the coding region of the corresponding gene. The RNA-specific probe may be derived from the genomic sequence of the transcribed portion of the selected gene or from the corresponding cDNA. If processing or distribution of the target RNA is being analyzed, intron-specific and exon-specific probes may be used to localize processed and unprocessed transcripts or to assess the extent of RNA processing. It is an important feature of the invention that the RNA-specific probe hybridizes to target RNA under conditions which minimize hybridization of the RNA-specific probe to the transcribed portion of the corresponding gene. This RNA-specificity is the basis of the ability of the methods to distinguish between the gene and its transcript.

Recent developments in high resolution in situ hybridization methods have demonstrated that the size of the nucleotide probes used for in situ hybridization has a significant effect on the level of background signal (J. B. Lawrence, C. A. Villnave and R. H. Singer. *Cell* 52, 61 (1988); U.S. Pat. No. 4,888,278). In this regard, it has been shown that the range of sizes of probe fragments is critical for non-isotopically labeled probes (e.g., biotin or digoxigenin), not the average fragment size. If a sufficient proportion of the nucleotides in the probe composition exceed a maximum critical length, background is significantly increased relative to the specific signal and sensitivity is reduced. When indirectly non-isotopically labeled probes are used in the present invention they therefore preferably comprise nucleotide fragments essentially all of which are less than about 1,000 nucleotides in length after labeling and more preferably less than about 200 nucleotides in length after labeling. If the nucleotides for probe preparations are produced by nick translation (which produces a broad range of nucleotide sizes), they are preferably sized prior to use in hybridizations to select those which are less than about 1,000 nucleotides long. Chemically synthesized oligonucleotides used as probes are also preferably synthesized according to these size criteria. For optimum sensitivity, the probes are preferably used in hybridizations at a relatively high concentration (about 100 times the amount of expected available RNA) to drive the kinetics of the reaction toward hybridization. In general, this will be a probe concentration of from about 0.2 μg/ml to about 20.0 μg/ml, preferably about 2.0 μg/ml. This increase in probe concentration over what was previously taught as appropriate in the prior art (M. E. Harper and L. M. Marselle. *Cancer Genetics Cytogenetics* 19,73 (1985); M. E. Harper, A. Ullrich and G. R. Saunders. *PNAS* 78,4458 (1981)) is in part the result of Applicants' discovery that high background signals are caused by large probe sizes, not high probe concentrations, as was previously believed. Control of probe size allows the probe concentration to be increased without increasing background, thereby providing more efficient hybridization kinetics. These parameters are described in U.S. Pat. No. 4,888,278 and by Lawrence, et al. (1988), the specifications of which are hereby incorporated by reference.

The DNA-specific probe and the RNA-specific probe are tagged with labels which are separately detectable to allow differentiation between the probe hybridized to the selected gene and the probe hybridized to the corresponding mRNA. Preferably, the labels are fluorescent moieties which emit light of different colors upon excitation, e.g., rhodamine (red) and fluorescein isothiocyanate (FITC, green). Those skilled in the art will appreciate that the invention is not limited to detection of a single gene/transcript pair using two colors of fluorescence and that using additional pairs of specific probes with appropriately distinguishable labels of different colors will allow detection of more than one gene in spatial correlation with its expression product. The label may be associated with or incorporated in the nucleotide probe using any of the methods known in the art (e.g., during chemical synthesis or nick translation of a cloned fragment; U.S. Pat. No. 4,711,955; C. Kessler, et al. *Biol. Chem. Hoppe-Seyler* 371,917 (1990)). The fluorescent labels are preferably added to the hybridized probe by means of a ligand included in the probe during synthesis via a ligand-derivatized deoxyribonucleoside triphosphate (dNTP). The ligand binds specifically to a receptor which carries the detectable label and thereby identifies the hybridized probe. Preferred ligands are haptens such as digoxigenin or biotin, both of which may be linked to dNTPs using procedures known in the art. The hybridized probe is then detected by specific binding of the associated ligand to its fluorochrome-conjugated receptor (preferably anti-digoxigenin or avidin) using staining methods appropriate for in situ hybridization.

The present methods are directed to the detection of nuclear RNAs. Cells prepared according to the inventive methods remain morphologically intact for the analysis, that is, hybridization of the nucleotide probes is performed within the permeabilized nucleus within the cytoplasm, not in cytogenetic preparations or nuclei fractionated from the cytoplasm. The following description is directed to analysis of cells, however, it will be apparent to those skilled in the art that tissue samples may be substituted for cells and analyzed accordingly. For most cell types, initial treatment to permeabilize the nuclear membrane is required to obtain penetration of the probe. An important feature of the invention is therefore the discovery of methods for permeabilizing the nucleus prior to hybridization which preserve the nuclear RNA, although these procedures may sacrifice the cytoplasmic RNA. A few cell types which are small and have minimal amounts of cytoplasm, such as lymphocytes and the rat PC-12 cells described below, do not require such treatment prior to hybridization. For permeabilization the cells may be placed in any buffer suitable for maintaining the integrity of the cells. However, the preferred buffer is cytoskeleton buffer described by E. G. Fey, G. Krochmalino and S. Penman. *Biol. Chem.* 102, 1654 (1986) previously used for isolation of nuclear ribonucleaoprotein matrix, with addition of an RNAse inhibitor. Permeabilization is preferably achieved by treatment of the cells for 10 sec. to 1 min. at 4° C. with a nonionic biological detergent such as NONIDET P-40 (an octylphenolethylene oxide) or TRITON (a polyoxyethylene ether). TRITON-X 100 is particularly preferred.

As permeabilization releases RNases which can degrade the targeted RNA, the detergent treatment and subsequent steps include an RNase inhibitor, for example Vanadyl sulfate complex or RNAsin. To further reduce degradation by RNases, the cells are kept cold prior to fixation. The RNase inhibitor is also added to antibodies and detection reagents that could contain RNase, e.g., anti-digoxigenin. The permeabilized cells are then fixed for about 1–15 min. with a fixative, usually in a buffer such as phosphate buffered saline (PBS). The fixative is selected such that the fixed cells remain penetrable by the probe and the nucleic acids are preserved and retained within the membrane. These fixatives restrict cross-linking and/or precipitation of proteins within the cell so that the matrix is less "hardened" to probe penetration but do not induce autofluorescence. In general, suitable fixatives are as described in U.S. Pat. No. 4,888,278 and J. B. Lawrence, et al. (1989) supra. A preferred fixative with these properties is paraformaldehyde, which is used at about 1–10% in PBS for about 5–30 minutes, preferably 5–15 min., to fix the permeabilized cells. The most preferred fixing conditions are about 4% paraformaldehyde for about 5 min. at room temperature. These treatments allow the cells to be permeabilized and fixed without destruction or substantial diffusion of targeted nuclear RNA, although cytoplasmic RNA may be lost. If desired, the cells may then be stored in 70% ethanol at 4° C. until hybridization. Storage may improve the results of the hybridization in certain cases, provided the cells are not stored for more than a few months.

Because nuclear mRNAs are generally very labile, it was unexpected that hybridization of an RNA-specific probe to RNA could be followed by denaturation and specific hybridization to DNA without loss of the RNA signal. In a first embodiment of the invention, the RNA-specific and DNA-specific probes are hybridized sequentially to the prepared cells. The sequential hybridization is most suitable for situations in which the targeted sequence is the same in both the RNA and the DNA or if the RNA target is particularly fragile (sequential hybridization reduces exposure of the RNA to harsh reaction conditions as compared to cohybridization). The RNA of the cells is hybridized first to the RNA-specific probe under conditions such that the DNA is not available for hybridization. This is preferably accomplished by providing hybridization conditions in which the DNA is not denatured (i.e., remains double stranded) and is therefore unavailable for hybridization to the single stranded probe. As the RNA is already single stranded, hybridization of the RNA-specific probe will then be specifically to the RNA. That is, the term "RNA-specific probe" refers to the fact that the selected hybridization conditions and protocol cause the probe to hybridize specifically to RNA. These conditions are most conveniently accomplished by adjusting the concentration of formamide in the hybridization buffer to below the level which will denature double-stranded DNA and avoiding elevated temperatures. Typically, the formamide concentration will be less than about 60%, more preferably about 50% in 2X saline sodium citrate buffer (SSC). The RNA-specific probe will generally be hybridized to the nucleic acid of the fixed cells for about 10 min.–20 hr., more preferably for about 2–16 hr., and most preferably for about 3–4 hr. at 37° C. If additional reagents are required to visualize the signal, as when the probe contains a hapten detectable by addition of a receptor conjugated to a label, they are then added to the hybridized cells under appropriate conditions to produce the detectable signal indicative of probe hybridization to RNA.

In some cases it has been observed that a diffuse RNA signal is produced which is not due to hybridization of the RNA-specific probe to DNA. Addition of $C_ot1$ DNA to the RNA-specific hybridization reaction eliminates or reduces this diffuse signal, which is believed to be due to the presence of repetitive elements in some RNAs which will hybridize to certain probes. This then allows the localized sites of specific RNA, correlating to gene expression, to be visualized.

Following hybridization of the RNA-specific probe to the RNA of the fixed cells, the cells are fixed a second time. This second fixing step serves to preserve and stabilize the signal from the RNA-specific probe during subsequent denaturation and hybridization of the DNA-specific probe. It is not yet known whether the second fixing step stabilizes the probe:RNA hybrid itself or in some other way preserves the probe label (and the signal ultimately detected) at the site of initial hybridization. In either case, it has been found that this step is important for maintaining the RNA signal at the site of transcription and preventing loss of signal at that site either by degradation, diffusion or some other mechanism. The second fixative is also preferably paraformaldehyde and the cells are preferably treated with about 1–10% paraformaldehyde for about 5–30 min. as above. The most preferred conditions for the second fixation are 4% paraformaldehyde for 10–15 min. at room temperature.

The double stranded DNA in the cells is then denatured prior to hybridization with the DNA-specific probe. Preferably, denaturation is accomplished by treatment with about 60–80% formamide at elevated temperature, more preferably about 70% formamide in 2X SSC at about 70° C. for about 2 min. The DNA-specific probe is then hybridized to the denatured nucleic acids of the cell for about 10 min. to 20 hr., more preferably about 2–16 hr. at 37° C. The DNA-specific signal is then developed by appropriate methods as are known in the art.

In a second embodiment, hybridization to DNA and RNA targets is performed in a single hybridization reaction (cohybridization) under DNA-denaturing conditions. This method reduces the number of steps and is useful when different sequences are being targeted in the DNA and RNA, but it may weaken the RNA signal when used for same-target-sequence hybridizations. However, if the target RNA is abundant in same-target-sequence hybridizations, some loss of signal can be tolerated without loss of utility. The cohybridization protocol is essentially the RNA hybridization portion of the sequential hybridization protocol but with denaturing conditions. The probes are added simultaneously to the permeabilized, fixed cells in which the nucleic acids have been denatured by treatment with 60–80% formamide, preferably 70% formamide, at about 70° C. After hybridization at about 37° C. for about 2 hr. to overnight, both probe signals are developed. $C_ot1$ DNA may be added to the hybridization to reduce diffuse signals from repetitive sequences if necessary.

The simultaneous hybridization methods of the present invention have for the first time allowed identification of the function of the previously observed RNA tracks as sites of transcription and processing. The methods fix the RNA at the site of transcription so that a specific mRNA can be spatially correlated with the gene from which it is transcribed. It is therefore not essential to perform simultaneous hybridization in every situation to assess transcriptional activity, i.e., it is not always necessary to visualize the gene at the same time as the transcript, as Applicants have established that the inventive staining methods fix the RNA at the corresponding gene. In such cases, only the RNA-specific probe may be used in the nondenaturing hybridization protocol as described above and the result observed for the formation of RNA tracks as an indication of gene expression.

The results of the foregoing hybridization procedure may be interpreted and analyzed either qualitatively, semi-quantitatively or quantitatively. The methods are useful for determining whether or not expression of a selected gene is occurring simply by observing the presence or absence of RNA tracks or foci. That is, the number and location of distinct foci or tracks of RNA can be used to determine the number and/or location of copies of a selected gene which are actively being expressed. Alternatively, using instrumentation or subjective methods of data analysis, the level of RNA fluorescence associated with expression of a selected gene can be used to quantify the amount of mRNA which is being transcribed relative to another gene or relative to a predetermined level of expression. For example, computerized digital image microscopy or densitometry of standard photographs as is known in the art are useful methods for quantitating fluorescence. Such quantitative and semi-quantitative analysis of the data is useful for determining over-expression or under-expression of a selected gene. The results of the instant transgene analysis suggest that at least a two-fold difference in gene expression is subjectively detectable, for example, by visual analysis of fluorescence levels directly in the microscope or on photographs.

The following experimental examples are presented to illustrate certain embodiments of the invention and are not to be construed as limiting the invention as defined by the appended claims.

EXAMPLE 1

RNA for the extracellular matrix glycoprotein fibronectin was localized in rat fibroblasts (RFL-6) and myoblasts (L6) using a 6.5 kb genomic probe derived from the gene sequence starting at about 6 kb from the transcription initiation site. The cells were grown and analyzed as monolayers on glass cover slips. Before hybridization, cells were treated three times (10–30 sec. each) with Hank's solution at room temperature, followed by a 10 sec wash with cytoskeleton buffer (CSK—100 mM NaCl, 300 mM sucrose, 10 mM PIPES, 3 mM $MgCl_2$, 1:20 vanadyl denosine complex) at 4° C. The cells were then permeabilized by treatment for 30 sec. with 0.5% Triton X-100 in CSK buffer at 4° C. and washed for 10 sec. with CSK buffer at 4° C. The permeabilized cells were fixed in 4% paraformaldehyde and 1X phosphate-buffered saline (PBS) for 5 min. at room temperature. Cells were stored in 70% ethanol at 4° C. until hybridization.

The prepared cell samples were dehydrated on the slides by sequential exposure to 70%, 95% and 100% ethanol and air dried. The probe was dried, resuspended in 10 μl of 100% formamide and denatured at 75° C. for 10 min. Ten μl of hybridization buffer (2 parts 50% dextran sulfate, 1 part 20X saline sodium citrate (SSC), 1 part BSA and 1 part Vanadyl complex) was added to the denatured probe and mixed to give a final concentration of 5 μg/ml of probe. The probe solution was applied to the slides and incubated at 37° C. for 3–4 hr. After hybridization, the slides were rinsed according to the following protocol: two 30 min. washes in 2X SSC, 50% formamide at 37° C. and one 30 min. wash in the same buffer at room temperature. The hybridized cells were washed for 10 min. in 4X SSC prior to staining with fluorescein-avidin for 1 hr. with 1% BSA, 4X SSC. The stained cells were rinsed for 15 min. in 4X SSC, 15 min. in 4X SSC, 0.01% TRITON X-100, and 15 min. in 4X SSC, then observed under the fluorescence microscope.

Up to 80% of the nuclei showed one or two distinct sites of intense fluorescence, indicative of hybridization of the probe to accumulated fibronectin nuclear RNA. This result was confirmed by controls showing that the hybridization was specifically to RNA, as alkaline hydrolysis of RNA with NaOH removed the nuclear signals. The controls also confirm that the DNA of the corresponding gene was unavailable for hybridization with the RNA-specific probe during the RNA hybridization protocol.

It was observed that the fibronectin RNA frequently accumulated in tracks up to 6 µm long which, in some cells, extended through several planes of focus. The length and orientation of the tracks with respect to the x, y and z axes were variable. Similar, apparently non-specific orientation of tracks was observed in experiments to determine the nuclear localization of six different viral and cellular precursor mRNAs.

Similar in situ hybridizations to the transcripts from the inducible gene for neurotensin in rat PC-12 cells was accomplished using a genomic probe spanning the 10 kb gene. The cells were induced to express neurotensin by the addition of nerve growth factor (100 ng/ml), 1 µM dexamethasone, 1 µM forskolin (Sigma Chemical Co., St. Louis, Mo.) and 10 mM LiCl. Because the PC-12 cells have little cytoplasm and are nonadherent on glass, they did not require detergent treatment but instead were spun from suspension onto cover slips for 5 min. at 500 rpm and fixed in 4% paraformaldehyde for 5 to 10 min. Hybridization was performed essentially as described for fibronectin RNA. Approximately 4 hours after induction, 42% of positive cells showed one distinct focus of intense nuclear fluorescence and 58% showed two foci. A diffuse, less intense signal was often apparent throughout the cytoplasm and nucleoplasm. Elongated tracks were not observed. Neither the cytoplasmic or nuclear signals were detectable in uninduced PC-12 cells.

To determine whether the concentrated RNA signals detected with genomic probes represented unprocessed transcripts, mature mRNA or excised introns, in situ hybridization was performed with fibronectin intron-specific and exon-specific (cDNA) probes. The intron-specific probe was labeled with digoxigenin and detected with a rhodamine-conjugated antibody to digoxigenin. The cDNA probe was labeled with biotin and detected with FITC-avidin in the same cells hybridized with the intron-specific probe. Both probes hybridized to just one or two focal sites within the nuclear interior and the two-color labeling demonstrated that both probes hybridized to the same nuclear foci, indicating the presence of unspliced transcripts. Similar results were obtained in parallel experiments for neurotensin RNA.

EXAMPLE 2

To determine whether RNA tracks and loci colocalized with the sites of transcription, hybridizations were performed to demonstrate the spatial relationship of the gene and the RNA. Fibronectin RNA was selected because of its more elongated track. This was accomplished by two-color simultaneous hybridization in situ to RFL-6 fibroblasts with a 4.3 kb digoxigenin-labeled probe for the nontranscribed 5' sequence immediately flanking the fibronectin gene (the DNA-specific probe) and a 6.5 kb biotin-16-dUTP-labeled probe for genomic DNA (the RNA-specific probe). The hybridized probes were detected by anti-digoxigenin antibody conjugated to rhodamine and avidin conjugated to FITC, respectively.

Both probes, plus 30–50 µg of $C_{o_t}1$ DNA, were added to a tube and dried. Slides with cells prepared as in Example 1 were rinsed in 1X PBS to remove ethanol and then rinsed in 2X SSC. The cells were denatured in 70% formamide, 2X SSC at 70° C. for 2 min., then dehydrated sequentially in 70%, 95% and 100% ethanol. The prepared slides were air dried. The dried probe mixture was resuspended in 10 µl of 100% formamide and the probes denatured at 75° C. for 10 min. 10 µl of hybridization buffer was added to the probe and mixed. The probe solution was applied to the slides and incubated for about 3–4 hr. or overnight. After hybridization, the slides were rinsed 30 min. in 2X SSC, 50% formamide at 37° C., 30 min. in 2X SSC at 37° C. and 30 min. in 1X SSC at room temperature. After an additional wash for 10 min. in 4X SSC, the cells were stained for 1 hr. with rhodamine-conjugated anti-digoxigenin and fluorescein-conjugated avidin in 4X SSC, 1% BSA at 37° C.

Figure 1A:
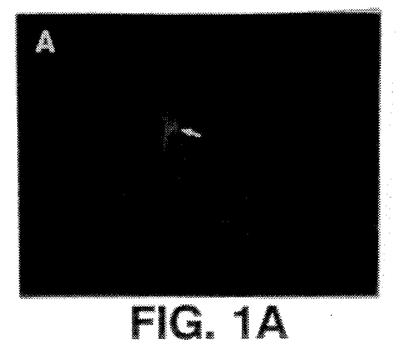
FIG. 1A and FIG. 1B show the nuclear location of the fibronectin gene and its primary transcripts, stained with fluorochrome labeled probes as described in Example 2.
Figure 1B:
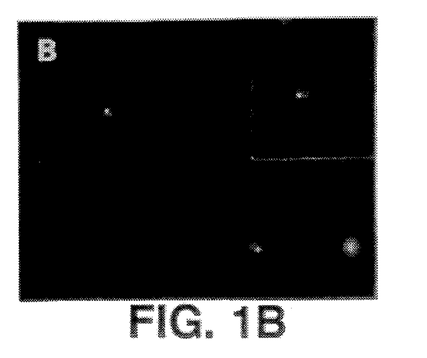

Photomicrographs of the stained cells were taken through a dual-band filter that allows precise alignment of red and green fluorescence. Alternatively, the image was captured by a charge coupled device (CCD) camera from separate filters superimposed and aligned with multicolor fluorescence beads as fiduciary markers. The gene and the RNA were found to be spatially coincident. For 86% of the gene signals detected there was an overlap between the signals from the gene and the RNA track. Furthermore, in 88% of the RNA tracks the gene was clearly positioned at or near one end (FIG. 1A and FIG. 1B). This polarity was apparent even within focal (non-elongated) accumulations of fibronectin RNA. These results show that RNA foci and tracks form directly at the site of transcription and indicate a structural polarity to RNA formation with the gene toward one end. Because the length of the gene is below the resolution of the light microscope the gene signal is seen as a point of fluorescence. For this reason the longer RNA formations observed are not equivalent to the "Christmas tree" of nascent transcripts synthesized along the DNA template as has been identified by electron microscopy for *Drosophila melanogaster* ribosomal DNA and the transcripts of amplified chorion genes, but instead appear as accumulations of many RNA molecules that extend well beyond the dimensions of the gene.

Figure 1C:
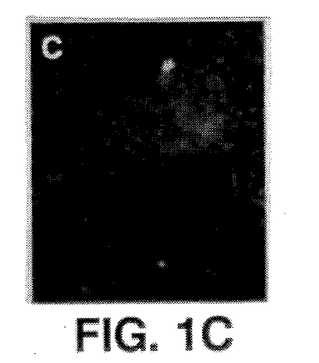
FIG. 1C shows the segmented RNA track described in Example 2, with the fluorescence of the exon-specific cDNA probe extending farther from the location of the gene than the fluorescence of the intron-specific probe.
Figure 2:
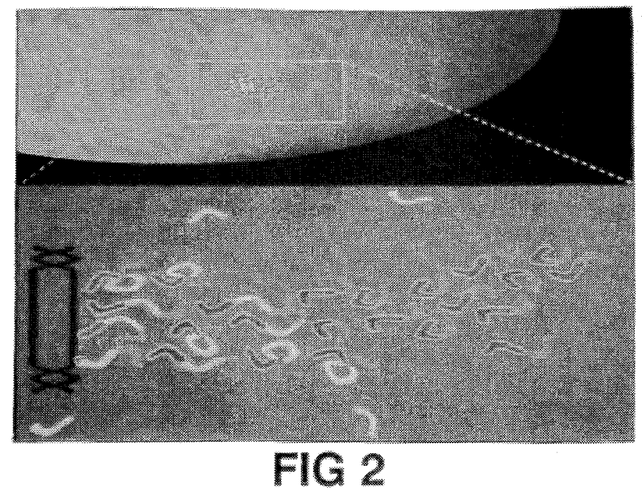
FIG. 2 is a schematic model for the ordered assembly of transcripts within the RNA track. Different stages of processing are concentrated in different areas along the processing track at varying distances from the gene.

Different hypotheses could explain RNA accumulation at the site of transcription. For example, it could represent a buildup of newly synthesized transcripts before transport elsewhere for processing or it could represent an "assembly line" of transcripts that undergo processing at or near the transcription site. Further two-color simultaneous hybridization studies with fibronectin cDNA and intron probes (cohybridization protocol) which allowed precise registration of the two colors demonstrated that the "assembly line" hypothesis is likely to be correct. In 84% of cells, hybridization with a digoxigenin-labeled cDNA probe (detected with anti-digoxigenin-rhodamine) formed longer tracks than those detected with a biotinylated intron-specific probe (detected with avidin-FITC). Within a single cell, the intron signal was generally confined to a smaller part of the track than the exon signal, creating the appearance of a two-color, segmented track (FIG. 1C). The segmented track was consistently observed with two different analytical methods: 1) a single filter set that allowed simultaneous visualization of red and green with no optical shift (Chroma Technology, Brattleboro, Vt.; C. V. Johnson, et al. (1991), supra; D. C. Tkechuk, et al. *Science* 250,559 (1990)), and 2) separate images captured by a cooled charge coupled device (CCD) camera that were aligned and superimposed. In control experiments in which a single probe was labeled with two colors, there was no separation of the red and green signals. The absence of intron sequences from a portion of the focus or track defined by the cDNA probe indicates that intron splicing occurs within the accumulation of RNA. Further, the results indicate that the splicing process is spatially ordered within the RNA track and that the RNA transcripts are physically associated with a nuclear substructure (FIG. 2). It was also observed with both genomic and intron probes that a less intense fluorescence was dispersed throughout the nucleoplasm, excluding the nucleolus, indicating that excised intron sequences apparently diffuse freely.

EXAMPLE 3

The distribution of fibronectin RNA relative to the transcript domains previously reported was investigated. Two different overlapping probes were used to define the transcript domains (K. C. Carter, et al. (1993), supra; K. C. Carter, et al. (1991), supra): oligo(dT) to detect total poly(A) RNA and an antibody to the spliceosome assembly factor SC-35 (X. D. Fu and T. Maniatis. Nature 343, 437 (1990)). A 2 kb digoxigenin-labeled cDNA probe for fibronectin RNA, detected using anti-digoxigenin-FITC, was hybridized first as described above. The biotinylated oligo(dT) probe (0.5 µg/ml) was then hybridized in 15% formamide and 2X SSC at 37° C. for 3 hr. and detected using rhodamine-avidin. Quantitative analysis of >100 cells by direct microscopic visualization through a dual-band filter or by superimposed computer images of optically sectioned cells captured from a CCD camera showed a nonrandom spatial relationship between fibronectin RNA foci or tracks and the larger transcript domains rich in poly(A) RNA and SC-35. Analysis was performed with optics that allow 0.5 µm z-axis resolution (Zeiss Neofluor 100, 1.4 numerical aperture). Approximately 88% of fibronectin RNA tracks or foci were associated with poly(A) RNA-rich transcript domains, with the majority (80%) either overlapping or in contact with the domain. Only about 8% of the tracks were completely within the domain and about 12% were not in contact. As the nuclear volume occupied by all of othe poly(A) domains in a given nucleus is estimated to be about 5% and specific RNA accumulations no more than about 1%, the frequency with which fibronectin RNA would spatially associate with these domains by random chance is small. The association of fibronectin RNA with the transcript domains therefore appears to be highly specific. The specificity of the association is further demonstrated by previous experiments showing that nontranscribed centromeric sequences are not associated with poly(A) containing domains.

The number, relative size and intensity of the signals for poly(A) RNA domains versus the signals for the specific RNA suggest that each transcript domain reflects the transcription and processing activity of several different genes. This is because the poly(A) RNA was detected with a small (55 nt) oligonucleotide end-labeled with only a few biotin molecules, whereas the fibronectin RNA is detected by much larger (1-6 kb) probes labeled throughout by nick translation. The amount of fluorescence generated per molecule with the poly(A) probe is therefore expected to be at least an order of magnitude less than that generated by the fibronectin mRNA probe. However, estimations of the relative intensity and size of individual poly(A) RNA domains indicated that the domains contain substantially more fluorescent signal than individual RNA foci or tracks do. This consideration, along with the observation that fibronectin RNA tracks only partially overlap the transcript domains, supports the conclusion that each transcript domain is likely to be the transcription and processing site of several RNAs.

The monoclonal antibody to SC-35 was allowed to bind at 37° C. for 60 min. and then detected using a rhodamine-conjugated donkey antibody to murine immunoglobulin (Jackson ImmunoResearch Labs.). The pattern of colocalization was similar for SC-35, but the fraction of fibronectin RNA tracks not in contact or overlapping a visible transcript domain increased to 32%, with 68% in contact with the domain. This is consistent with the observation that SC-35 forms a smaller inner core in the domain, so that some tracks may overlap the periphery of poly(A) domains without contacting the SC-35 core. Optical sectioning of several cells in 0.2 µm optical steps indicated that the fibronectin RNA accumulations did not extend to the nuclear envelope but were within the nuclear interior.

EXAMPLE 4

Figure 3A:
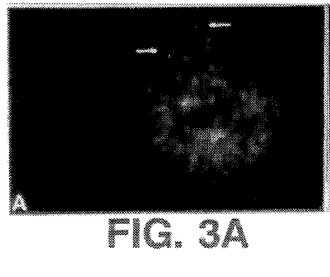
FIGS. 3A–3C show the parental (red, arrows) and vector-associated (yellow-green) transgene copies of collagen gene.
Figure 3B:
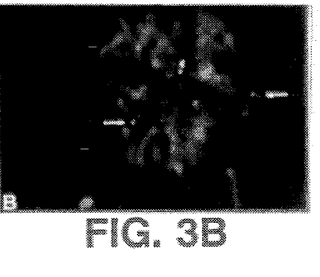
Figure 3C:
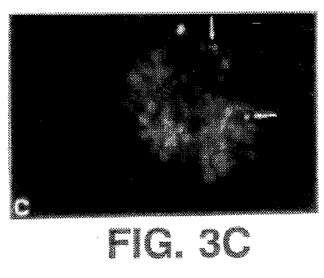

Fluorescence in situ hybridization according to the invention was used to detect expression of multiple copies of the M. spretus collagen gene in transgenic mouse cells, associated with an integrated pYAC151 vector. First, fluorescence in situ hybridization to genomic DNA was used to confirm that the transgene was carried at a single chromosome location. The digoxygenin labeled Col1a1 probe (detected with rhodamine) generated a single hybridization signal in the parental cells which was also seen in the transfected clones. This signal corresponded to the endogenous Col1a1 gene on chromosome 11 (FIG. 3A). A second collagen specific hybridization signal, which was also labeled by the vector probe, was seen in each of the transfected cell lines but not in the parental cells (FIGS. 3B and 3C). The signal was localized close to the centromere of a large chromosome in one clone and close to the telomere of a smaller chromosome in another clone. The vector and donor Col1a1 sequences therefore colocalize to a unique chromosomal site in the two transfected cell clones and, together with Southern blot analyses, are consistent with each transgene being physically intact.

Figure 3D:
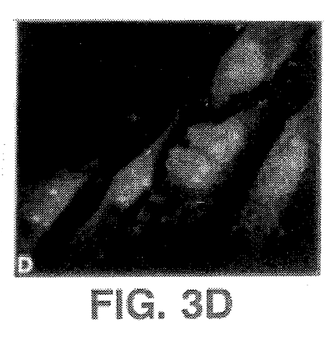
FIGS. 3D–3F show single probe hybridization to collagen RNA, detected with either fluorescein (D & F) or rhodamine (E).
Figure 3E:
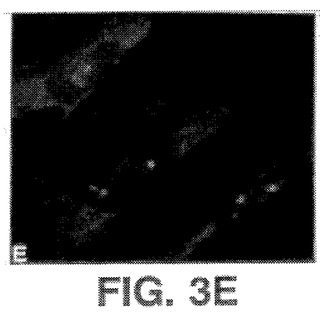
Figure 3F:
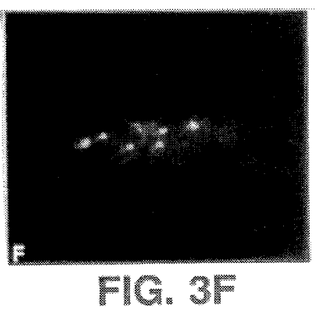
Figure 4A:
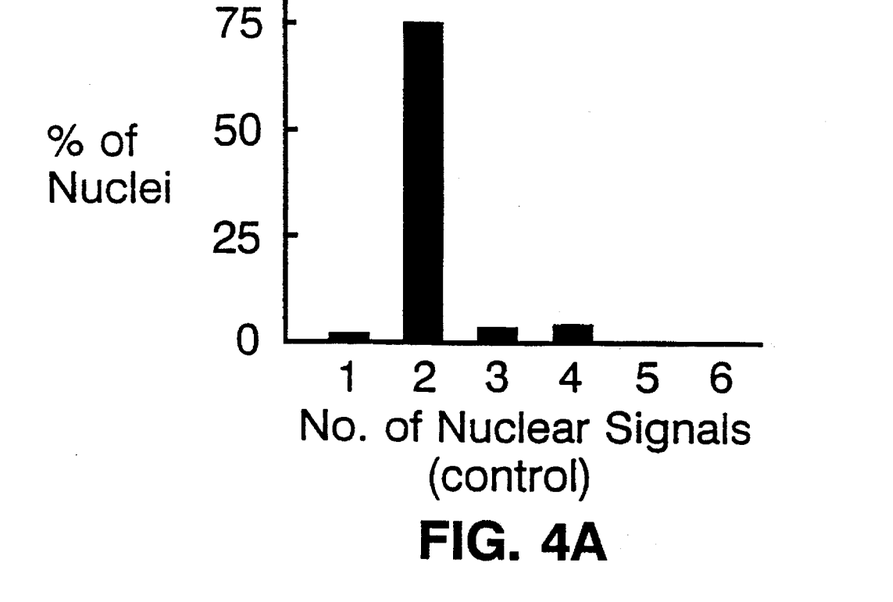
FIGS. 4A (control) and 4B (transgene) illustrate the results of Example 4 in histogram form, quantitating the number of nuclear RNA signals from the collagen gene transcribed in normal versus transgenic mice.
Figure 4B:
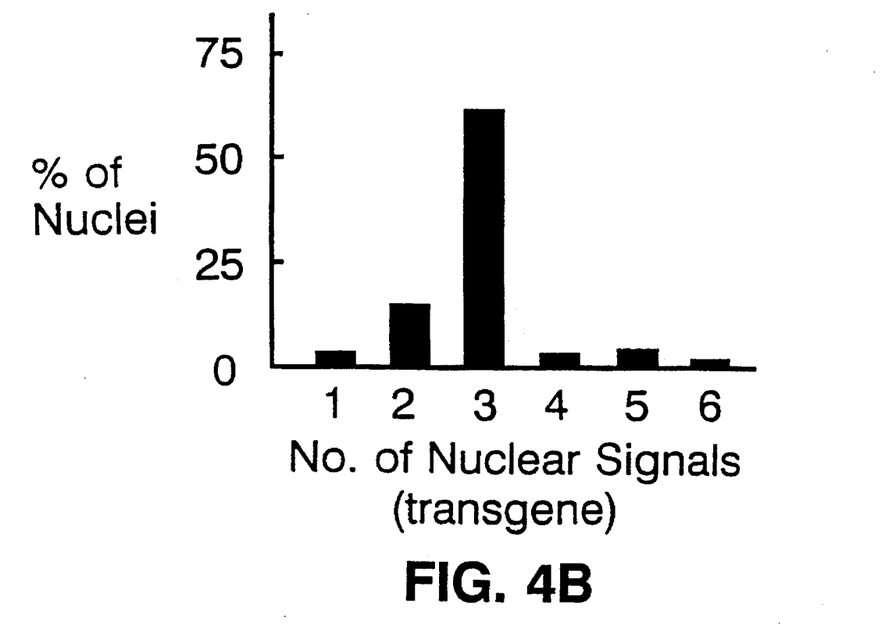

To demonstrate expression of the YAC transgene, primary dermal fibroblasts were prepared from control and transgenic animals and assayed for expression of α1(I) using fluorescent in situ hybridization. Four cell samples were isolated and hybridized to an RNA-specific nucleotide probe (the genomic probe) as described in Example 1 for hybridization to RNA but not DNA. In control cells, 78% of the population showed two large foci or tracks of nuclear RNA, indicating two sites of transcription (FIG. 3D). Only 5% showed three tracks. In contrast, analysis of cells from transgenic animals demonstrated that in the majority of cells (61–66%) there were three easily detectable collagen RNA tracks, demonstrating that collagen RNA was being produced at three distinct sites, corresponding to the three copies of the gene (FIG. 3E and FIG. 3F). These results are illustrated in histogram form in FIG. 4.

Confirmation that the third nuclear RNA signal was produced from the transgene sequence was achieved by simultaneous hybridization of collagen nuclear RNA and the 11 kb YAC vector DNA. Metaphase spreads were simultaneously hybridized (sequential hybridization protocol) to a 24 kb genomic probe corresponding to the Col1a1 collagen gene (detected by fluorescein-avidin) and to an 11 kb probe corresponding to the pYAC15 1 vector (detected by anti-digoxygenin-rhodamine). RNA-specific hybridization to the genomic probe was performed as in Example 1 but instead of observing the stained slides after the final rinse in 4X SSC, the cells were fixed a second time in 4% paraformaldehyde for 10-15 min. at room temperature. The fixed cells were rinsed in 1X PBS for 10 min. followed by a 10 min. wash in 2X SSC. The DNA-specific YAC probe was dried, resuspended and denatured in the same way as the RNA-specific probe in Example 1. The nucleic acids in the prepared cells were denatured in 70% formamide, 2X SSC at 70° C. for 2 min., dehydrated sequentially in 70%, 95% and 100% ethanol, and air dried. The probe solution was applied to the slides and incubated at 37° C. overnight. Following hybridization, the slides were rinsed and stained as described in Example 1 using anti-digoxygenin-rhodamine for detection of DNA. The slides were then mounted in anti-bleach mounting medium (Pheneyline dimine, Sigma Chemical Co., St. Louis, Mo.) and observed under the fluorescence microscope.

Figure 3G:
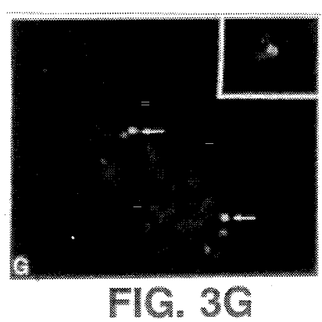
FIG. 3G and FIG. 3H show the results of sequential hybridization first to collagen RNA (green) and then to vector sequences (red) as described in Example 4.
Figure 3H:
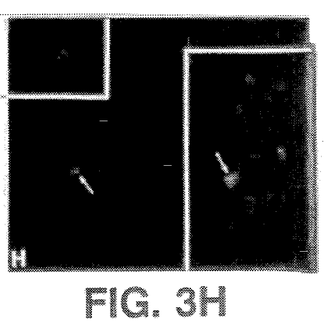

In cells from transgenic animals only, one collagen RNA track (labeled with fluorescein) was tightly spatially associated with DNA from the YAC transgene vector (labeled with rhodamine) (FIG. 3G and FIG. 3H). This association was observed in over 95% of cells and demonstrated that the RNA track was correlated with expression of the transgene. No vector sequences were detected in the control. It was also observed that when a larger RNA track was present (in about 48% of cells analyzed) it showed significant correlation with expression of the transgene rather than the endogenous gene (96% of cells). These results demonstrate that not only is the collagen transgene expressed, it is expressed at a level which is equivalent to or greater than the endogenous sequences. Using the present in situ hybridization methods for detecting transcription of specific, selected genes, the level of expression of the gene can also be determined by quantitating the level of fluorescence associated with the RNA track or focus.

What is claimed is:

1. An in situ hybridization method for simultaneously detecting in a cell nucleus a DNA sequence associated with a selected gene and mRNA transcribed from within the selected gene, comprising the steps of:
   (a) permeabilizing the cell nucleus while minimizing mRNA degradation;
   (b) fixing the cells a first time, with a fixative such that the nucleus remains penetrable by labeled probes, and the nucleic acids are preserved in place;
   (c) hybridizing the fixed cells a first time, under conditions that do not denature DNA, with an RNA-specific probe able to hybridize to an mRNA transcript from the selected gene without substantial hybridization to other RNA molecules present in the cell, said RNA-specific probe bearing a first label;
   (d) fixing the cells a second time, to preserve during a second hybridizaton RNA-probe hybrids formed during the first hybridization;
   (e) denaturing the nuclear DNA in the cells;
   (f) hybridizing the fixed cells a second time with a DNA-specific probe able to hybridize to a DNA sequence associated with the selected gene, without substantial hybridization to non-selected sequences, said DNA-specific probe bearing a second label distinguishable from the first label; and
   (g) simultaneously detecting said first label on said RNA-specific probe as a focus or track, and said second label on said DNA-specific probe as a point, said focus or track and said point being within about 2 μm of each other;
   wherein said DNA sequence associated with the selected gene comprises chromosomal nucleotide sequences on the same chromosome and within approximately 2 μm of the selected gene from which said mRNA is transcribed.

2. The method according to claim 1, wherein the first label and second label are fluorescent moieties that emit light of different colors upon excitation.

3. The method according to claim 1, wherein the permeablization step involves a nonionic detergent.

4. The method according to claim 1, wherein the first fixation step involves paraformaldehyde.

5. The method according to claims 1, wherein the conditions for the first hybridization include formamide at a concentration less than about 60% and a temperature not higher than about 37° C.

6. The method according to claim 1, wherein the second fixation step involves paraformaldehyde.

7. An in situ hybridization method for simultaneously detecting in a cell nucleus a DNA sequence associated with a selected gene and mRNA transcribed from within the selected gene, comprising the steps of:
   (a) permeabilizing the cell nucleus while minimizing mRNA degradation;
   (b) fixing the cells with a fixative such that the nucleus remains penetrable by labeled probes, and the nucleic acids are preserved in place;
   (c) hybridizing the fixed cells, under conditions that denature DNA, simultaneously with:
      (1) an RNA-specific probe able to hybridize to an mRNA transcript from within the selected gene without substantial hybridization to other RNA molecules present in the cell, said RNA-specific probe bearing a first label; and
      (2) a DNA-specific probe able to hybridize to the DNA sequence associated with a selected gene, without substantial hybridization to non-selected sequences, said DNA-specific probe bearing a second label distinguishable from the first label; and
   (d) simultaneously detecting said first label on said RNA-specific probe as a focus or track, and said second label on said DNA-specific probe as a point, said focus or track and said point being within about 2 μm of each other;
   wherein said DNA sequence associated with a selected gene comprises chromosomal nucleotide sequences on the same chromosome and within approximately 2 μm of the selected gene from which said mRNA is transcribed.

8. The method of claim 1 or 7, wherein said probes are selected from the group consisting of:
   (a) probes specific for a maternal allele within the selected chromosomal locus; and
   (b) probes specific for a paternal allele within the selected chromosomal locus.

* * * * *